US007763255B2

(12) United States Patent
Shaish et al.

(10) Patent No.: US 7,763,255 B2
(45) Date of Patent: Jul. 27, 2010

(54) **THERAPEUTIC USES OF *DUNALIELLA* POWDER**

(75) Inventors: Aviv Shaish, Yechiel (IL); Dror Harats, Ramat Gan (IL)

(73) Assignees: Nikken Sohonsha Corporation, Hashima (JP); Tel Hashomer Medical Research Infrastructure and Services Ltd., Tel Hashomer (IL)

( * ) Notice: Subject to any disclaimer, the term of this patent is extended or adjusted under 35 U.S.C. 154(b) by 0 days.

(21) Appl. No.: 11/822,786

(22) Filed: Jul. 10, 2007

(65) Prior Publication Data

US 2008/0019997 A1 Jan. 24, 2008

Related U.S. Application Data

(62) Division of application No. 10/668,601, filed on Sep. 24, 2003, now Pat. No. 7,264,813.

(51) Int. Cl.
*A61K 36/05* (2006.01)
(52) U.S. Cl. .................................. 424/195.17
(58) Field of Classification Search ........................ None
See application file for complete search history.

(56) References Cited

U.S. PATENT DOCUMENTS

| 4,915,965 | A | 4/1990 | Tanaka |
| 5,190,970 | A | 3/1993 | Pan et al. |
| 5,304,575 | A | 4/1994 | Beck |
| 5,972,881 | A | 10/1999 | Heyman et al. |
| 6,362,221 | B1 | 3/2002 | Clark et al. |
| 6,365,186 | B1 * | 4/2002 | Huval et al. |
| 6,680,387 | B2 | 1/2004 | Druzgala et al. |
| 6,914,073 | B2 | 7/2005 | Boulos et al. |

FOREIGN PATENT DOCUMENTS

| FR | 279561 | 1/2001 |
| IN | 189624 | 3/2003 |
| JP | 10248526 | 9/1998 |
| JP | 2003180387 | 7/2003 |
| WO | 98/57636 | 12/1998 |
| WO | 01/03693 | 7/2000 |
| WO | 02/12233 | 2/2002 |

OTHER PUBLICATIONS

Fábregas, J. et al. J Gen. Appl. Microbiol (1994), 40: 553-540. Decrease of plasma cholesterol with the marine microalga *Dunaliella tertiolecta* in hypercholesterolemic rats.*
Levy, Y et al. Journal of Nutritional & Environmental Medicine (1995); 5: 13-22. Effect of dietary supplementaion of different beta-carotene isomers on lipoprotein oxidative modification.*
Dachet, C et al. Arterosclerosis (1995); 113: 1-9. Effect of gemfibrozil on the concentration and composition of very low density and low density liproptein subfractions in hypertriglyceridemic patients.*

Chen, Z et al. Arteriosclerosis, Thrombosis, and Vascular Biology. 2001;21:372. Troglitazone inhibits atherosclerosis in apolipoprotein E-knockout mice: pleiotropic effects on CD36 expression and HDL.*
H. Takashi et al., *Decrease of the plasma cholesterol level by administration of Dunaliella extract in exogenous hypercholesterolemic mice*, 28 J. Aichi Med. Univ. Assoc. 249 (2000). XP-002314572 abstract, database EMB-2000378484.
Y. H. Itoh et al., *Inhibitory effect of Dunaliella 'beta!-carotene extracted from Dunaliella bardawil on plasma lipids of rats: Effect on lipid synthesis and excretion phase in Triton-induced intrinsic hyperlipidemia*, 28 J. Aichi Med. Univ. Assoc. 263 (2000). XP002314573 abstract, database EMB-2000378485.
Ito Yoko et al., *Inhibitory Effects of Administration Natural .BETA.-Carotene Derived from Dunaliella bardawil on Plasma Cholesterol Concentrations in Exogenous Hyperlipidemic Mice*, 29 Japanese J. App. Physiol. 91 (1999). XP-002314574 abstract, database STN 990497471.
Jianxiang Huang et al., *The effects of beta-carotene from Dunaliella salina on experimental atherosclerosis in quails*, 39 Qingdao Daxue Yixueyuan Xuebao 441 (2003). XP-002314575 abstract, database STN 2004:313857.
Sumi Ryo et al., *Effects of Natural .Beta.-carotene Contained Dunaliella Hard Capsule on Human Hyperlipidemia*, 66 Pharmacometrics 37 (2004). XP-002314576 abstract, database STN 1040472647.
Yishai Levy et al., *Dietary supplementation of a natural isomer mixture of beta-carotene inhibits oxidation of LDL derived from patients with diabetes mellitus*, 44 Annals of Nutrition and Metabolism 54 (2000). XP009042880.
Avron et al., *Dunaliella: Physiology, Biochemistry, and Biotechnology*, in CRC Press (Chapter 9) 206 (1992).
Ben-Amotz et al., *Bioavailability of a Natural Isomer Mixture as Compared with Synthetic all-trans-β-carotene in Rats and Chicks*, 119 J. Nutr. 1013 (1989).
Mukherjee et al., *Sensitization of diabetic and obese mice to insulin by retinoid X receptor agonists*, 386 Nature 407 (1997).
C. Day, *Thiazolidinediones: a new class of antidiabetic drugs*, 16 Diabetic Medicine 179 (1999).
Levy et al., *Dietary supplementation of a natural isomer mixture of beta-carotene inhibits oxidation of LDL derived from patients with diabetes mellitus*, 44 Annals of Nutr. & Metabolism 54 (2000).
I. Yoko et al., *Decrease of blood lipid levels in hyperlipidemia by administration of Dunaliella powder (dry powder of Dunaliella bardawil)*, 30 Nippon Rinsho Seiri Gakkai Zasshi 217 (2000). (Translation included).
Levy et al., *Effect of dietary supplementation of different beta-carotene isomers of lipoprotein oxidative modification*, 5 J. Nutr. & Environ. Medicine 13 (1995).

* cited by examiner

*Primary Examiner*—Michele Flood
(74) *Attorney, Agent, or Firm*—The Nath Law Group; Susanne M. Hopkins

(57) ABSTRACT

A method for treating a disease selected from diabetes mellitus and atherosclerosis, and a method for reducing triglycerides and/or increasing HDL cholesterol levels in the plasma of a subject. The method comprises administrating to a subject an effective amount of crude *Dunaliella* powder, optionally together with an activator of nuclear receptors.

8 Claims, 10 Drawing Sheets

US 7,763,255 B2

THERAPEUTIC USES OF *DUNALIELLA* POWDER

FIELD OF THE INVENTION

This invention relates to the use of crude *Dunaliella bardawil* powder in the treatment of a number of conditions including high triglyceride and low high-density lipoprotein (HDL) cholesterol levels, atherosclerosis and diabetes.

REFERENCES

The following is a list of references believed to be pertinent as a background to the present invention:
1. Ben-Amotz, A. and Shaish, A., Carotene Biosynthesis in *Dunaliella*: Physiology, Biochemistry and Biotechnology, Ed. Avron, M. and Ben-Amotz., 9:206-16, 1992.
2. U.S. Plant Patent No. 4,511, issued Mar. 18, 1980.
3. U.S. Pat. No. 4,199,895, issued Apr. 29, 1980.
4. Ben-Amotz, A., Mokady, S., Edelstein, S. and Avron, M., Bio-availability of a natural isomer mixture as compared with synthetic all-trans beta-carotene in rats and chicks, *J. Nutrition*, 119:1013-1019, 1989.
5. Day, C., Thiazolidinediones: a new class of antidiabetic drugs *Diabetic Med.*, 16:179-192, 1999.
6. Mukherjee, R., Davies, P. J. A. et al., Sensitization of diabetic and obese mice to insulin by retinoid X receptor agonists. *Nature*, 386:407-410, 1997.

BACKGROUND OF THE INVENTION

Two strains of *Dunaliella*, a unicellular, biflagellate, wall-less green alga, are capable of producing very large amounts of β-carotene, *Dunaliella salina* Teod. and *Dunaliella bardawil*[1]. *D. bardawil* is a halotolerant alga whose β-carotene content comprises about 50% all-trans-β-carotene with the remainder composed mostly of 9-cis β-carotene and a few other β-carotene isomers[2]. A process has been described for cultivating *D. bardawil* so as to obtain algae containing up to about 5% by weight of β-carotene[3]. Later developments of the process increased the percentage to more than 8%. It has been shown that the natural isomer mixture of β-carotene which is accumulated in the alga *Dunaliella bardawil* is accumulated in fatty tissues of rats and chicks to an extent which is about 10 fold higher than that observed by feeding the synthetic all-trans β-carotene[4].

Various carotenoid-enriched *Dunaliella* commercial products are available such as Betatene™ (produced by the Henkel Corp., Germany) and Nutrilite™ (Amway, Inc., U.S.A.). These products are oil extracts of carotenoids from *Dunaliella*.

Retinoids are essential for a living organism for vision, cellular growth, differentiation, and to maintain the general health of the organism. 9-cis-retinoic-acid and all-trans-retinoic-acid are produced in the body by the cleavage of β-carotene (BC). The retinoid nuclear receptors, also known as orphan receptors RAR and RXR, have distinct physiologic properties by activating transcriptional factors. All-trans retinoic-acid binds to RAR but not to RXR, while 9-cis retinoic-acid binds to RXR, which plays a key role in important biological processes.

The activation of nuclear receptors is essential to cell metabolism, especially with respect to lipids and glucose. Several nuclear receptors have been implicated in cholesterol homeostasis. These receptors include: the liver X receptors (LXRa/NR1H3 and LXRb/NR1H2) and farnesoid X receptor (FXR/NR1H4) that are bound and activated by oxysterols and bile acids, respectively. LXR and FXR form obligate heterodimers with RXR that is activated by 9-cis retinoic acid and synthetic agonists (termed rexinoids). It was recently found that the activation of RXR by its ligands can affect two central processes of cholesterol metabolism: I. Cholesterol absorption in the intestine (activation of RXR/FXR heterodimer repressed cholesterol 7α-hydroxylase (CYP7A1) expression, resulting in decreased bile acid synthesis and cholesterol absorption). II. Reverse cholesterol transport from peripheral tissues (activation of RXR/LXR heterodimer inhibited cholesterol absorption and induced reverse cholesterol transport in peripheral tissues).

The following nuclear receptors are known to form heterodimers with RXR and hence, can be potentially activated by 9-cis retinoic acid administration: thyroid hormone (TRa/b); vitamin D (VDR); fatty acid/eicosanoids (PPARα/βγ); oxysterols (LXRa/b); bile acids (FXR); pregnanes/bile acids/xenobiotics (PXR); androstanes/xenobiotics (CAR).

Fibrates (clofibrate, fenofibrate, bezafibrate, ciprofibrate, beclofibrate and gemfibrozil) are currently recommended for the treatment of patients with hypertriglyceridemia (high plasma TG). The treatment of hypertriglycerdemia results in decreased plasma levels of triglyceride-rich lipoproteins. HDL cholesterol levels are usually increased when the baseline levels are low. The increase in HDL cholesterol is usually concomitant with increased levels of the HDL apolipoprotein A-I and A-II. In addition, fibrates reduce the atherogenic apoC-III-containing particles, effect post-prandial lipemia and some fibrate lower plasma fibrinogen and CRP levels.

As a consequence of their effect on lipid metabolism, fibrates have been shown to affect specific lipoprotein disorders such as in combined hyperlipidemia, primary hypertriglyceredemia, type III dysbetalipoprotenemia, and non-insulin dependent diabetes mellitus (NIDDM).

Fibrates are considered to be well tolerated, with an excellent safety profile. A low toxicity has been reported in almost every organ system. Fenofibrate treatment revealed low frequency of side effects. Long-term administration revealed no effect on peroxisome proliferation in human liver and no evidence for carcinogenesis. Clinically relevant interaction of fibrates with other anti-hyperlipedemic drugs include rhabdomyolysis and decreased bioavailability when combined with some bile acid sequestrants. Potentiation of the anticoagulant effect of coumarin may cause bleeding.

Fibrates mediate at least part of their effects by peroxisome proliferator-activated receptor α (PPAR-α). Upon activation with fibrates, PPARs heterodimerize with another nuclear receptor, the 9-cis retinoic acid receptor (RXR). The dimer binds to specific response elements, termed peroxisome proliferator response elements (PPREs) and regulates gene expression.

Low plasma levels of high-density lipoprotein (HDL) and high triglyceride (TG) plasma levels are risk factors for atherosclerosis. Low levels of plasma HDL cholesterol, apolipoprotein AI (apoA-I) and high levels of triglycerides (TG) are associated with increased risk for atherosclerosis, the major cause of morbidity and mortality in Western societies. A recent study showed that the rate of coronary events is reduced by 22 percent by raising HDL cholesterol levels and lowering the plasma TG levels in patients treated with the fibrate gemfibrozil.

Several modes of action were proposed for the fibrate beneficial effects on atherosclerosis: Induction of lipoprotein lipolysis by reducing apoC-III levels and/or by increasing lipoprotein lipase activity. Induction of hepatic fatty acid (FA) uptake by the induction of FA-transporter protein and acyl-CoA synthetase. Decrease apoB and VLDL production.

Reduction of hepatic TG production by induction of peroxisome (in rodents only) or mitochondrial β-oxidation pathway and inhibition of FA synthesis. Most important, fibrates increase the production of apoA-I and apoA-II in the liver, which probably contribute to the process of reverse cholesterol transport.

Type 2 diabetes mellitus is a serious health problem. It arises when resistance to the glucose lowering effects of insulin combines with impaired insulin secretion to raise the levels of glucose in the blood beyond the normal range. Thiazolidinediones are a new class of antidiabetic agents that improve insulin sensitivity and reduce plasma glucose and blood pressure in subjects with type 2 diabetes[5]. The drugs bind and activate PPARγ that binds to DNA as heterodimers with a common partner, retinoid X receptor (RXR) to regulate transcription. RXR agonists have been shown to function as insulin sensitizers, markedly decreasing serum glucose, triglycerides and insulin in obese mice[6].

WO 93/24454 describes a carotenoid composition derived from *Dunaliella* algae in which the β-carotene content is predominantly 9-cis β-carotene. There is no mention of any medical applications.

U.S. Pat. No. 5,219,888 (Katocs) discloses a method to increase plasma HDL levels for the treatment and prevention of coronary artery disease by administrating a therapeutic amount of the retinoids all trans-retinoic acid and 9-cis-retinoic acid.

U.S. Pat. No. 5,948,823 discloses use of a substantially crude *Dunaliella* algae preparation in protecting mammals against the detrimental effects of medical and nuclear irradiation.

WO 97/10819 teaches a new treatment for non-insulin dependent diabetes mellitus by administration of RXR agonists and optionally, peroxisome proliferation activated receptor gamma agonists.

WO 99/50658 identifies compounds which modulate nuclear receptor activity, used for treating e.g. cancer, cardiovascular disease, osteoporosis, diabetes, postmenopausal disorders and inflammatory conditions.

WO 2001119770 reveals new retinoid X analogs, useful as retinoid X receptor modulators for lowering blood glucose levels, for modulating lipid metabolism and in treatment of e.g. diabetes, obesity, cardiovascular diseases and breast cancer.

U.S. Pat. Nos. 5,972,881 and 6,028,052 (Heyman) disclose methods and compositions for the treatment of non-insulin dependent diabetes using an RXR agonist together with a PPARγ agonist.

WO 03/027090 provides novel retinoid compounds that have selectivity as RXR agonists, and are effective in reducing blood glucose and maintaining body weight, thus being useful for the treatment of diabetes (NIDDIM) and obesity.

Colagiuri S. and Best, *J. Lipid-lowering therapy in people with type 2 diabetes*. Current Opinion in Lipidology (2002) 13:617-623, teaches that lipid powering with statins and fibrates is effective in improving cardiovascular disease outcome in diabetes.

Levy, Y. et al. *Dietary supplementation of a natural isomer mixture of Beta-carotene inhibits oxidation of LDL derived from patients with diabetes mellitus*. Nutrition & Metabolism (2000) 44:54-60, describes experiments in which *Dunaliella bardawil*-derived β-carotene was supplemented to the diet of diabetic patients. The dietary supplementation normalized the enhanced LDL susceptibility to oxidation in these patients.

SUMMARY OF THE INVENTION

It is an object of the invention to provide a method for treating patients suffering from diabetes, low plasma HDL and/or high plasma TG and/or atherosclerosis.

The present invention provides by one of its aspects, a method for treating a disease selected from diabetes mellitus and atherosclerosis comprising administrating to a subject an effective amount of crude *Dunaliella* powder.

The present invention also provides by another aspect a method for reducing triglycerides and/or increasing HDL cholesterol levels in the plasma of a subject comprising administrating to the subject an effective amount of crude *Dunaliella* powder.

In accordance with another aspect of the invention there is provided a medicament for use in treating diabetes mellitus, low plasma HDL and/or high plasma TG and/or atherosclerosis, comprising an effective amount of a substantially crude *Dunaliella* algae preparation.

In accordance with a further aspect of the invention, there is provided the use of an effective amount of a substantially crude *Dunaliella* algae preparation in the preparation of a pharmaceutical composition for use in treating diabetes mellitus, low plasma HDL and/or high plasma TG and/or atherosclerosis The active ingredient in accordance with the invention is a substantially crude *Dunaliella* algae preparation, typically dried *Dunaliella* algae. The *Dunaliella* algae are preferably *Dunaliella bardawil*.

The terms "treating" or "treatment" in the present specification should be understood as including both the curing of the disease, as well as bringing about an improvement in the pathological symptoms of the disease. The terms may also include prevention of the diseases. These terms also relate to the potential to inhibit both the initiation and progression of atherosclerosis and to the reduction of inflammation, thereby inhibiting and preventing complications of the disease.

An "effective amount" should be understood as an amount or dose of the active ingredient which is sufficient to achieve the desired therapeutic effect, i.e. treatment of the indicated diseases. The effective amount depends on various factors including the severity of the disease, the administration regimen, e.g. whether the preparation is given once or several times over a period of time, the physical condition of the subject; etc. The artisan should have no difficulties, by minimal experiments, to determine the effective amount in each case.

The term "atherosclerosis" includes all types of the disease including calcified plaques, non-calcified plaques, fibrocalcified plaques and others. The term "diabetes" includes all types of diabetes, in particular type 2 diabetes mellitus.

In a preferred embodiment, the crude *Dunaliella* powder is administered together with one or more activators of nuclear receptors. The activators of nuclear receptors are preferably peroxisome proliferator-activated receptor α and γ(PPAR α and PPAR γ) agonists, such as fibrates and thiazolidinediones. Non-limiting examples of fibrates are clofibrate, fenofibrate, bezafibrate, ciprofibrate, beclofibrate and gemfibrozil. Non-limiting examples of thiazolidinediones are AVANDIA® (rosiglitazone maleate), troglitazone, BRL 49653, pioglitazone, ciglitazone, WAY-120,744, englitazone, AD 5075, darglitazone and rosiglitazone.

The crude *Dunaliella* powder is preferably administered orally, for example in an encapsulated form.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EMBODIMENTS OF THE INVENTION

Methods and Materials

All of the human studies described below employed capsules containing *Dunaliella* powder prepared as follows.

*Dunaliella bardawil* (hereinafter "Db") was grown and cultivated in large body open salt water ponds of 50,000 m$^2$ to obtain algae comprising 8% by weight of β-carotene (hereinafter "BC") at an approximately 1:1 ratio of all-trans and 9-cis BC (4,9). The algae were harvested by dislodging centrifuges into a concentrated paste. The paste was washed to remove the salt and sterilized, and then spray dried to yield Db powder comprising approximately 8% BC and less than 5% moisture. The powder was packaged in capsules of 250 mg algae containing 20 mg of BC each together with all of the natural components of the algae. The BC of the capsules retains the original 1:1 ratio of isomers. The capsules are packaged in vacuum closed blisters which have a shelf life of up to three years. For the animal studies the Db powder was mixed with the diet to give 8% of *Dunaliella* powder in the feed.

EXAMPLE I

The aim of the first experiment was to study the effect of a combination treatment of fibrates and a crude *Dunaliella* powder-rich diet on plasma apoAI and HDL cholesterol levels.

Six month old male littermates, transgenic human apoAI mice on the background of C57BL/6 mice were used (Rubin E M, Ishida B Y, Clift S M, Krauss R M. (1991) Proc Natl Acad Sci U S A. January 15; 88 (2):434-8, *Expression of human apolipoprotein A-I in transgenic mice results in reduced plasma levels of murine apolipoprotein A-I and the appearance of two new high density lipoprotein size subclasses*). The mice contain the liver-specific enhancer of the human apo A-I gene promoter necessary to drive hepatic apo A-I expression. The mice (n=24) were divided into four groups (n=6 in each group) and fed daily with a standard diet (Koffolk, Israel Diet no. 19510) ad libitum. The first group (control) was administrated with phosphate buffered saline (PBS). The second group (Fibrate) was administrated with ciprofibrate (Lipanor, CTZ, Israel), 30 mg/Kg body weight, in PBS. The third group (*Dunaliella*) was supplemented with PBS and crude *Dunaliella* powder. The fourth group was supplemented with ciprofibrate and crude *Dunaliella* powder, which provided ~4 g of 9-cis-β-carotene per one Kg of the diet. The mice were sacrificed after 4 weeks of treatment.

Figure 1:
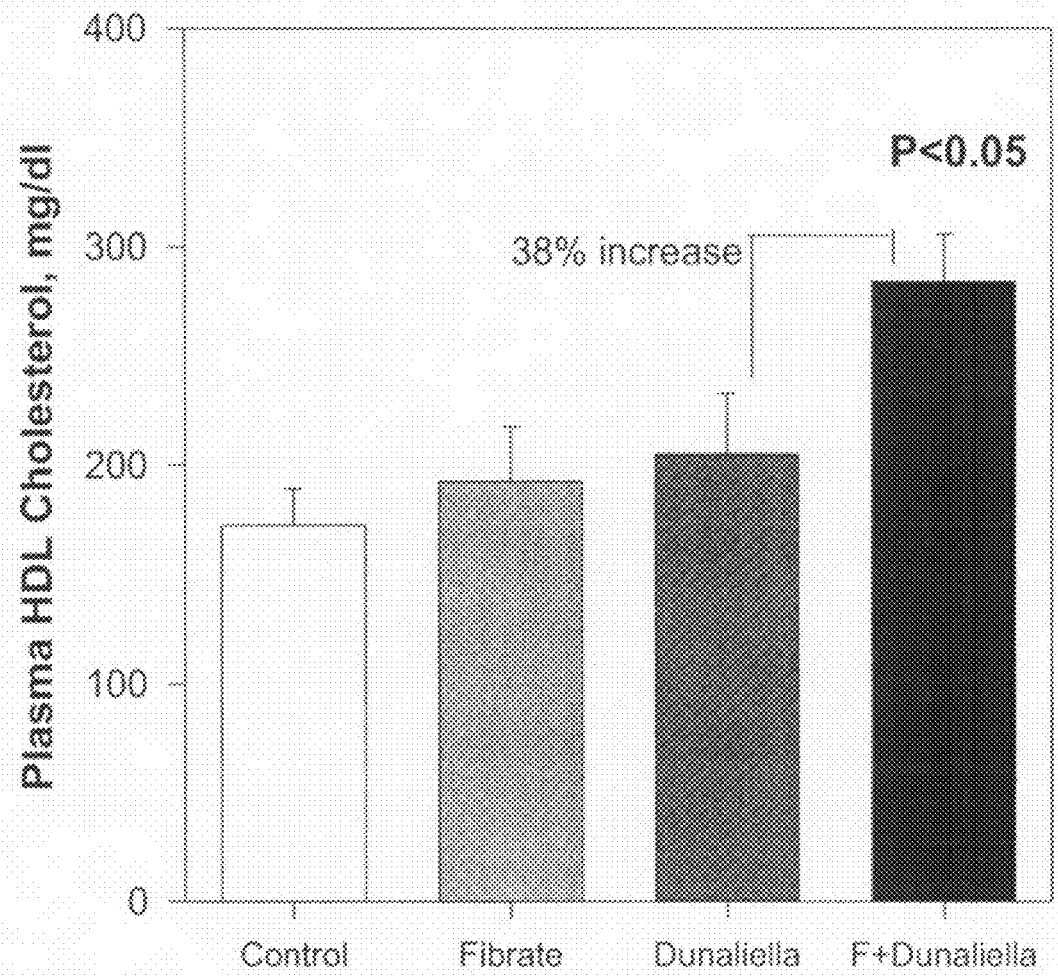
FIG. 1 illustrates the effect of a combination treatment of fibrates and crude *Dunaliella* powder on plasma HDL cholesterol levels in human apoAI transgenic mice.

The results (FIG. 1) showed that plasma HDL cholesterol levels reached the highest levels in mice treated with both fibrate and crude *Dunaliella* powder ($p<0.05$ all pairwise multiple comparison procedures, "control" group versus "ciprofibrate plus crude *Dunaliella* powder group"). The lowest level was detected in the control group, 408±42 mg/dl, and the highest in the combination of ciprofibrate and crude *Dunaliella* powder treated group, 535±71 mg/dl. A similar trend, although not statistically significant, was observed in apoAI plasma levels.

EXAMPLE II

Figure 2:
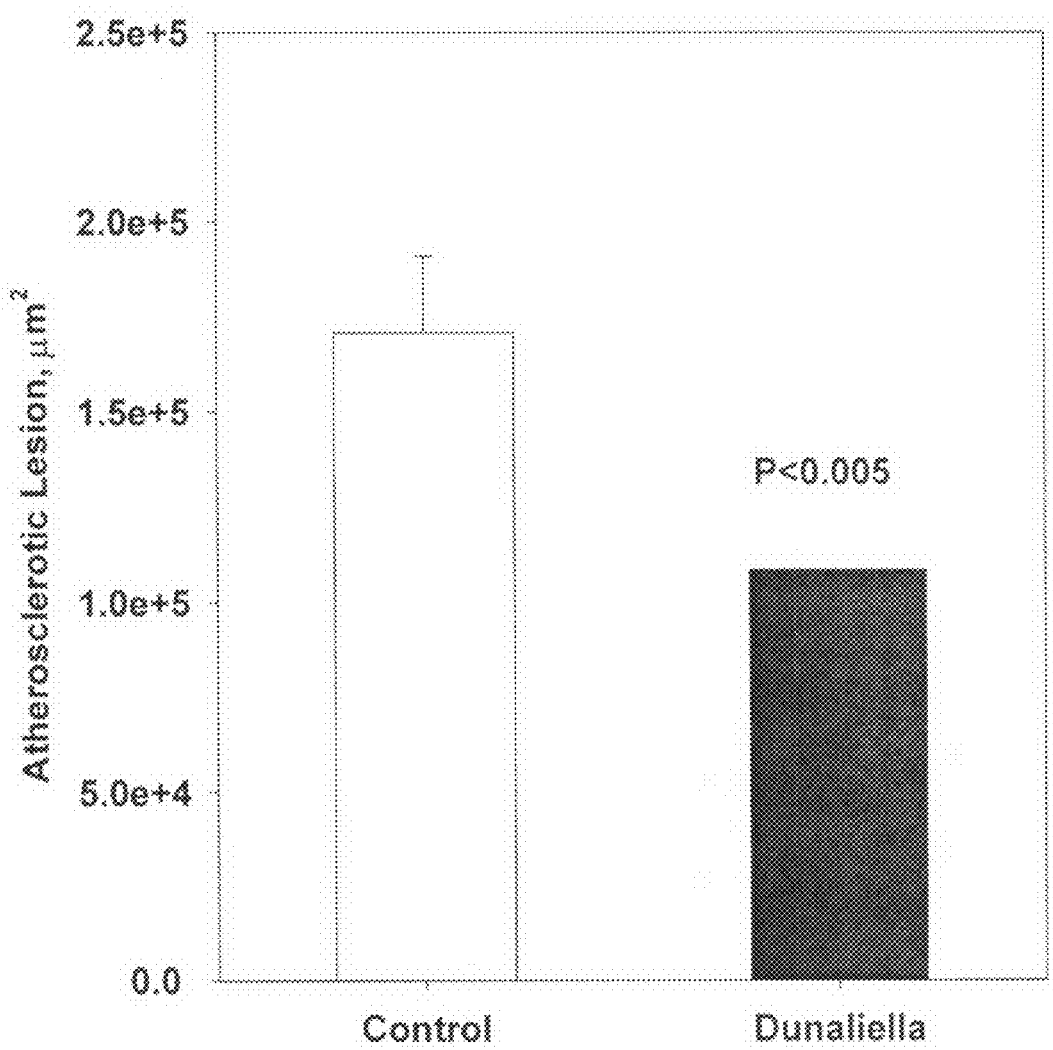
FIGS. 2-4 show the effect of crude *Dunaliella* powder on atherogenesis by the size (area) of atherosclerotic lesions at the aortic sinus in male apoE-deficient mice (FIGS. 2 & 3) and in male LDL receptor-deficient mice (FIG. 4)

To test the effect of *Dunaliella* on atherogenesis, male apoE-deficient mice (n=10) were fed with standard chow diet as defined above, supplemented with 8% of crude *Dunaliella* powder for 6 weeks. A control group (n=10) received chow diet alone. Atherosclerosis, determined by the lesion size at the aortic sinus, was 34% lower in the group of mice treated with crude *Dunaliella* powder than in the control group of mice (FIG. 2).

EXAMPLE III

Figure 3:
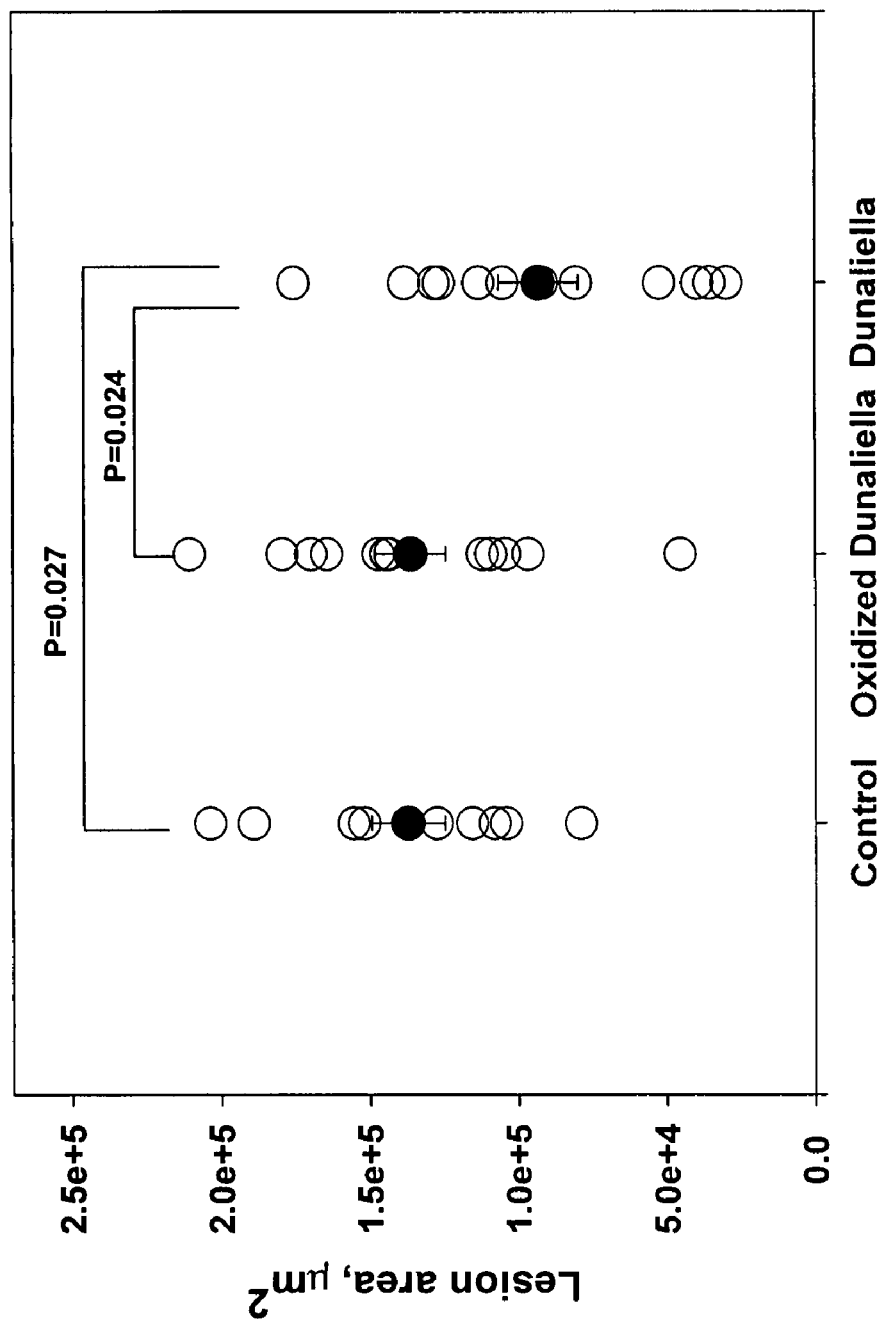

To test the effect of *Dunaliella* powder on atherogenesis, male apoE-deficient mice (n=13) were fed a standard chow diet supplemented with 8% *Dunaliella* powder for 8 weeks. A second group (n=12) was treated with oxidized *Dunaliella* powder, containing no β-carotene, while the control group (n=12) received chow diet alone. Atherosclerosis, determined by the lesion size at the aortic sinus, was 33% lower in *Dunaliella* treated group than in control group, $p=0.027$ (FIG. 3). In contrast, oxidized *Dunaliella* powder did not affect atherogenesis.

EXAMPLE IV

Figure 4:
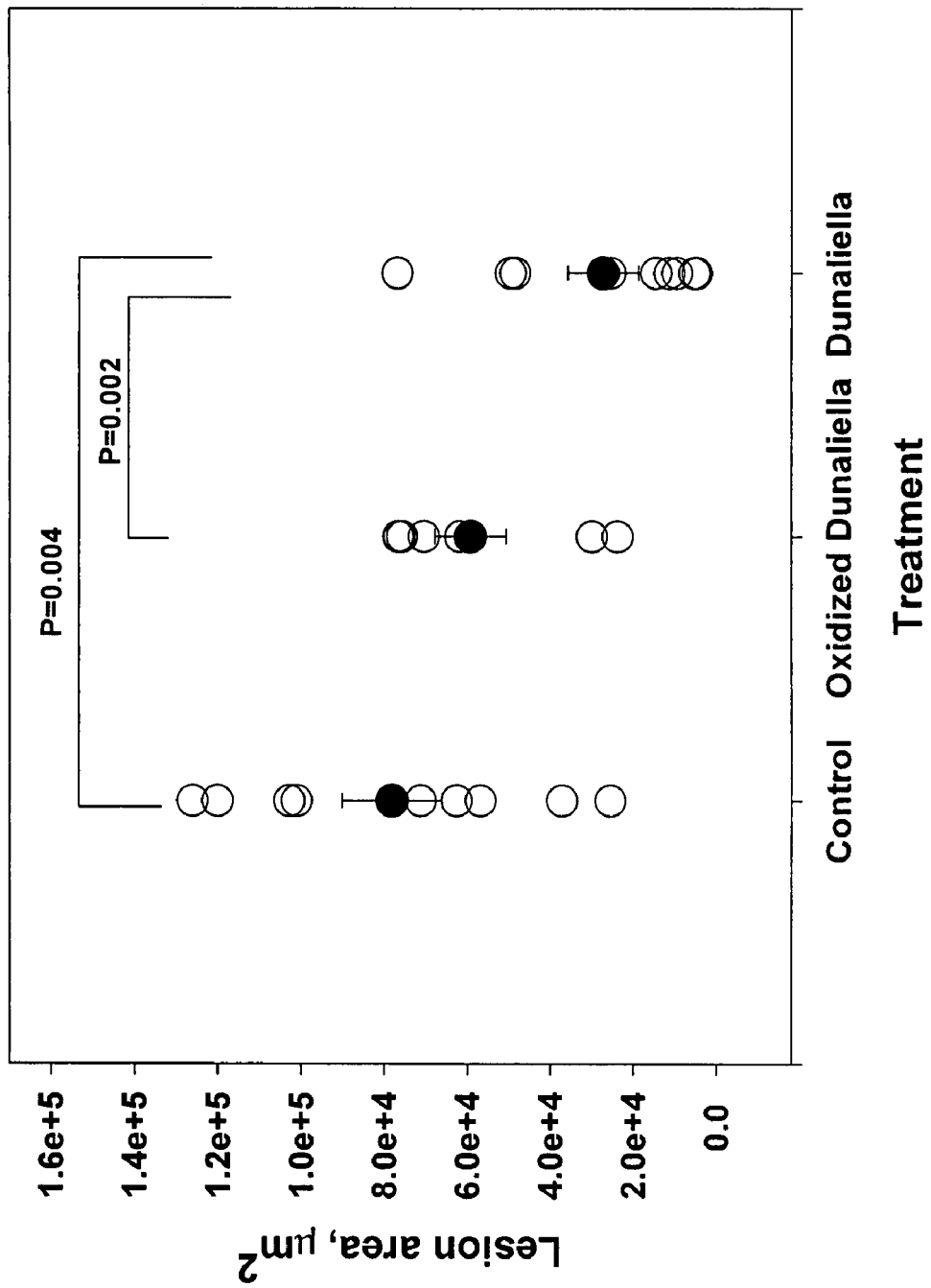

To test the effect of *Dunaliella* on atherogenesis, male LDL receptor-deficient mice (n=10) were fed a standard chow diet supplemented with 8% *Dunaliella* powder for 3 weeks followed by 7 weeks of Western diet. A second group was treated with oxidized *Dunaliella* powder (n=10) and control group (n=10) received chow diet followed by Western diet, alone. Atherosclerosis, determined by the lesion size at the aortic sinus, was 65% lower in *Dunaliella* treated group than in control group, $p=0.004$ (FIG. 4). In contrast, oxidized *Dunaliella* powder did not affect atherogenesis.

EXAMPLE V

Figure 5:
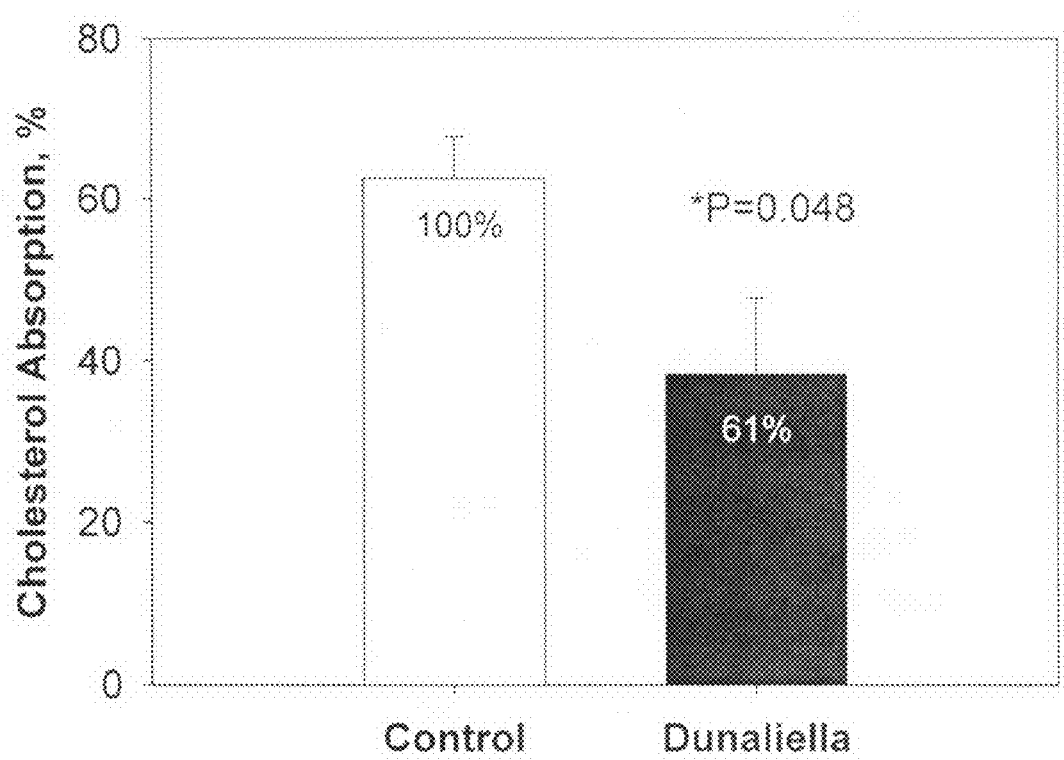
FIG. 5 illustrates measurement of cholesterol absorption in apoE-deficient mice.

Cholesterol absorption was measured by a fecal dual-isotope method, which measures the ratio of fecal excretion of $^3$H-sitostenol (which is not absorbed) to $^{14}$C-cholesterol (which is variably absorbed). The apoE-deficient mice were divided into 2 groups, the group of mice treated with *Dunaliella* was administrated with 8% of crude *Dunaliella* powder in chow diet for 3 weeks (n=6) and a control group (n=6) received chow diet alone. Administration of crude *Dunaliella* powder to apoE-deficient mice resulted, (similarly to previously described RXR agonists) in inhibition of cholesterol absorption (FIG. 5).

EXAMPLE VI

The aim of the human trial was to study the effect of the combination of fibrate and crude *Dunaliella bardawil* powder in patients with low HDL (<35 mg/dl) and high TG levels (>250 mg/dl).

At the first stage the patients (n=20) received fibrates (ciprofibrate or bezafibrate) for at least 3 months. At the second stage of the study the patients received 4 pills of crude *Dunaliella* powder according to the invention, 2 pills with breakfast and 2 pills with dinner, to provide a total daily uptake of 80 mg of β-carotene. Plasma lipid profile was detected after each stage of the study.

Figure 6:
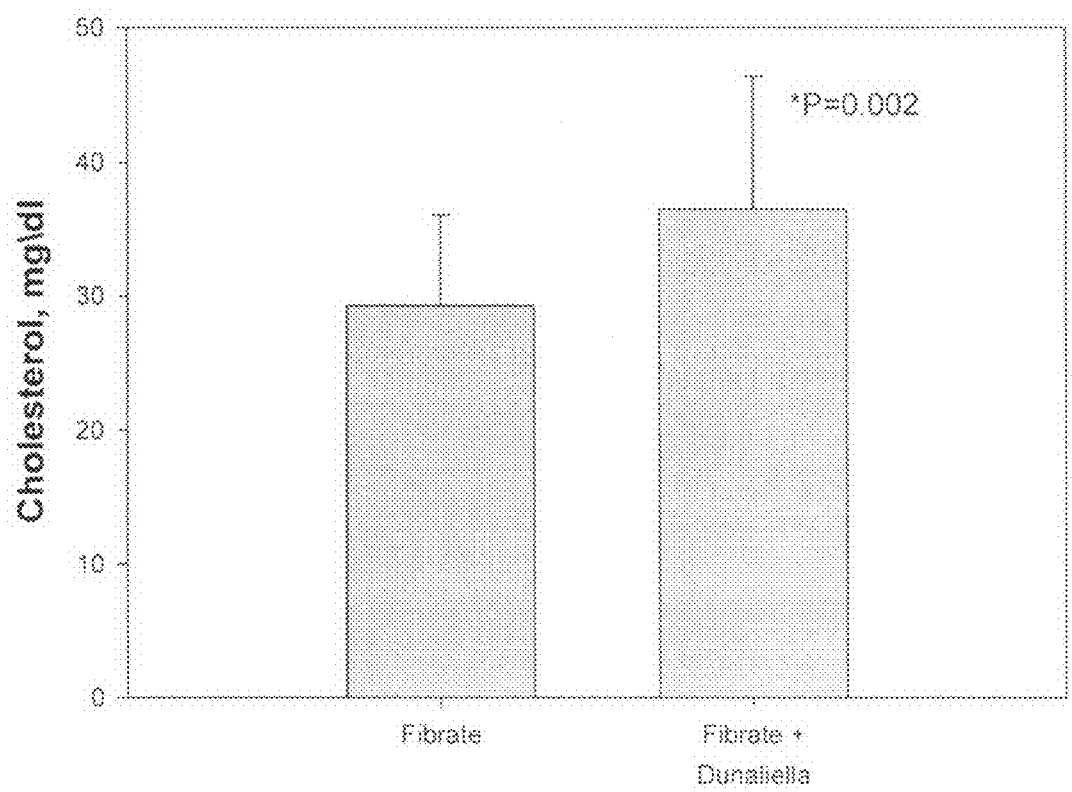
FIG. 6 shows HDL-cholesterol levels in patients receiving a dual treatment of fibrate with and without crude *Dunaliella* powder.

The results (FIG. 6) show that plasma HDL levels were significantly (p=0.002, paired t-test) higher after the combined treatment of fibrate and crude *Dunaliella* powder treatment in comparison to fibrate alone (29.3±6.8 mg/dl versus 36.5±9.9 mg/dl, respectively; a 24.5% increase).

A similar trend, although not significant (p=0.35) was observed in plasma apoAI levels, 120.9±15.2 versus 128.4±28.2 in fibrate and fibrate together with β-carotene, respectively. These findings suggest that the combined treatment affects both apoAI synthesis and the process of reverse cholesterol transport.

EXAMPLE VII

To test the effect of *Dunaliella* on Diabetes, male LDL R-\-mice (n=30) were fed a Western diet (42% calories from fat) in order to induce Diabetes. After 4 weeks of Western diet feeding, the mice were divided into 6 groups (n=5 in each group) and were fed Western diet fortified by rosiglitazone (0.02% of the diet, weight/weight), crude *Dunaliella* powder (8% of the diet, weight/weight) or 9-cis retinoic acid (24 nmol/mouse×day). The treatments lasted 4 weeks.

The 8% *Dunaliella* powder provided ~1.5 nmol 9-cis retinoic acid/mouse×day. This calculated amount is based on conversion of β-carotene to vitamin A (27 molecules provide 1 molecule of vitamin A and on the ratio of retinoic acid to vitamin A which is about 1 molecule of retinoic acid to 300 molecules of retinol, retinal and retinoic acid).

The following groups were included:
1. Control, Western diet alone. (Control)
2. 9-cis retinoic acid (RA)
3. Rosiglitazone (Rosi)
4. *Dunaliella* powder 8% (Dun)

Results

Figure 7:
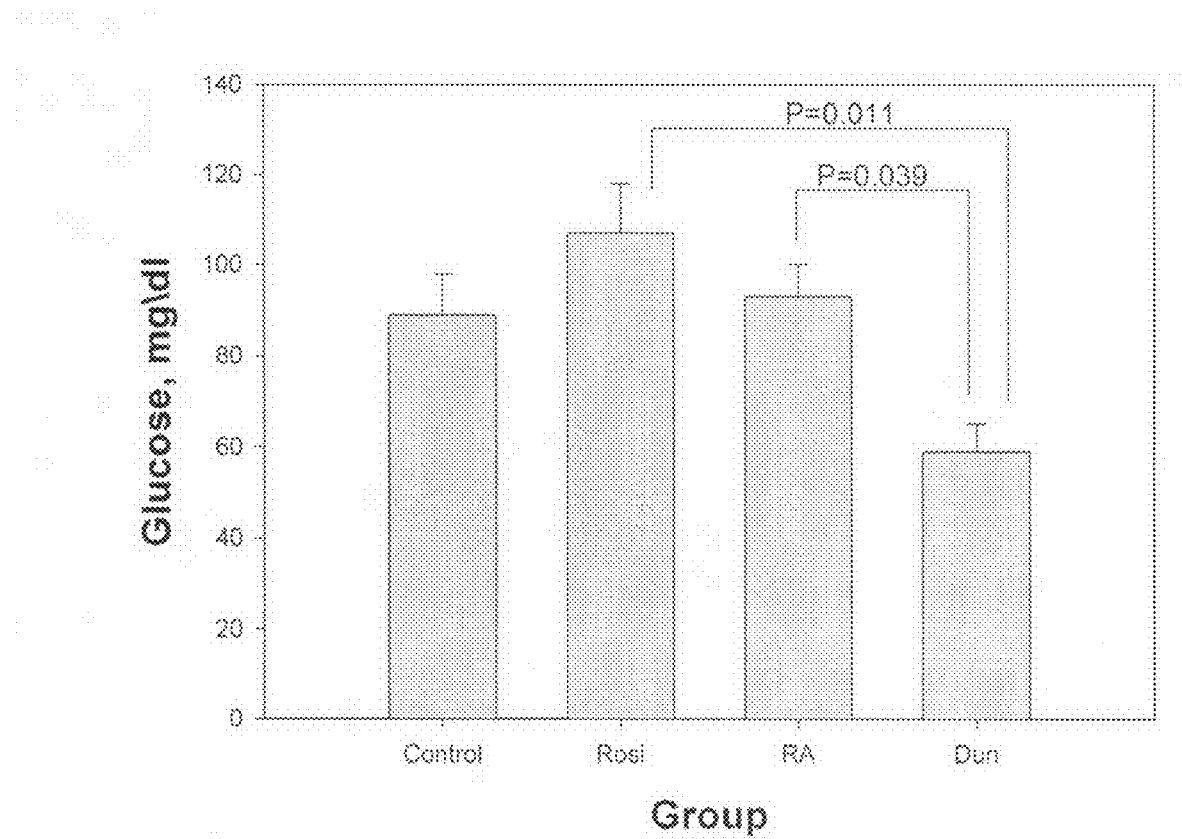
FIGS. 7-10 show plasma insulin, plasma glucose, plasma triglycerides and plasma cholesterol levels in male LDL R-\- mice with induced diabetes.
Figure 8:
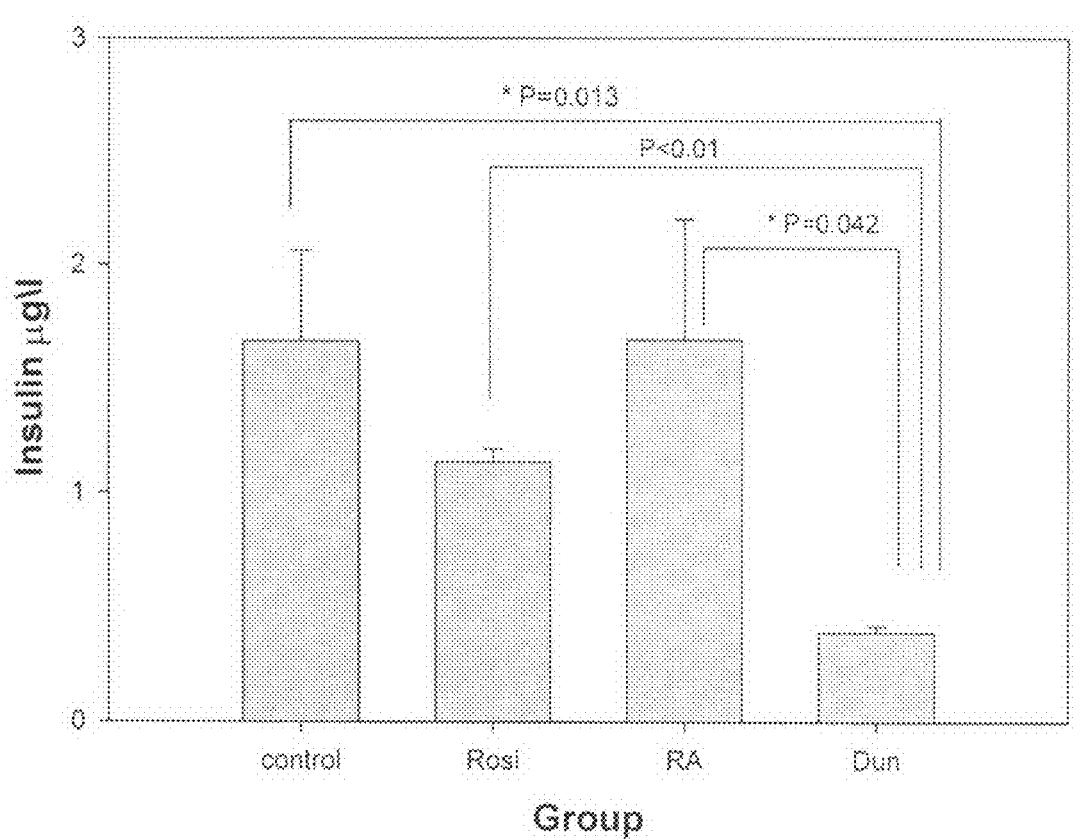
Figure 9:
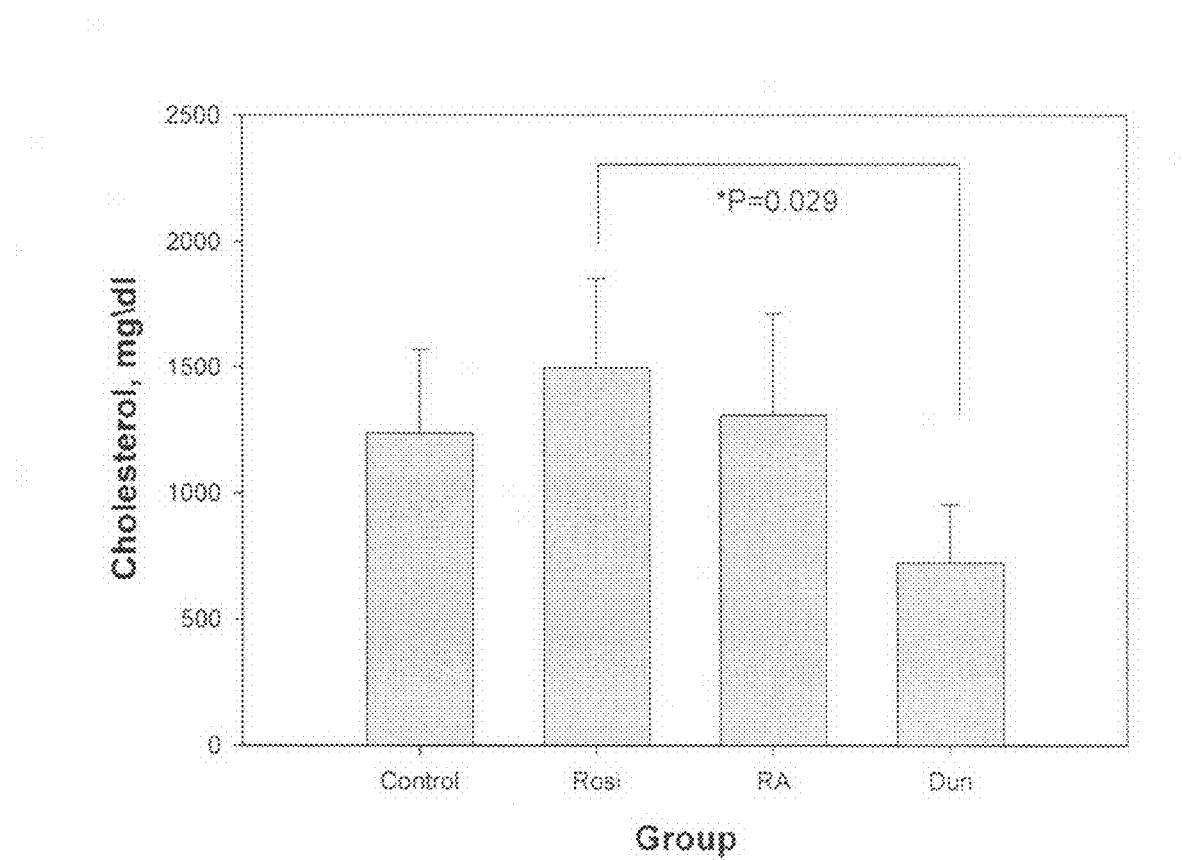
Figure 10:
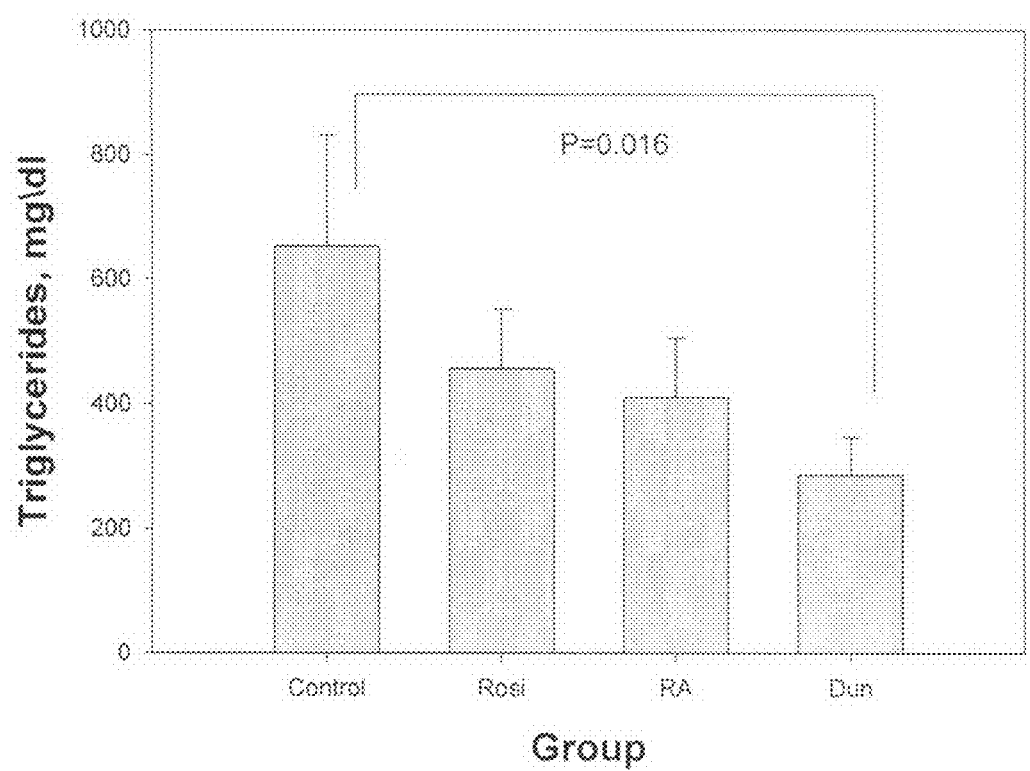

*Dunaliella* treatment reduced both plasma glucose and insulin levels as compared to rosiglitazone and control groups (FIGS. 7 and 8). Moreover, *Dunaliella* treatment reduced plasma cholesterol and TG levels significantly comparing to rosiglitazone group (FIGS. 9 and 10). On the other hand, 9-cis retinoic acid did not affect plasma insulin and glucose levels and their levels in *Dunaliella* group were significantly lower. The results demonstrate that *Dunaliella* powder can reduce plasma insulin and glucose levels more efficiently than 9-cis retinoic acid or rosiglitazone in LDLR-/-mouse model.

The invention claimed is:

1. A method for increasing high-density lipoprotein (HDL) cholesterol levels in the plasma of a subject having a low HDL cholesterol level, comprising:
   administering an effective amount of dried *Dunaliella* algae to the subject having a low HDL cholesterol level, thereby increasing the HDL cholesterol level in the subject in a statistically significant manner; and wherein the dried *Dunaliella* algae is administered together with one or more activators of nuclear receptors.

2. The method according to claim 1, wherein the activators of nuclear receptors are peroxisome proliferator-activated receptor α or γ (PPARα or PPARγ) agonists.

3. The method according to claim 2, wherein the PPARα or PPARγ agonists are selected from the group consisting of fibrates and thiazolidinediones.

4. The method according to claim 3, wherein the fibrates are selected from clofibrate, fenofibrate, bezafibrate, ciprofibrate, beclofibrate and gemfibrozil.

5. The method according to claim 3, wherein the thiazolidinediones are selected from the group consisting of AVANDIA® (rosiglitazone maleate), troglitazone, BRL 49653, pioglitazone, ciglitazone, WAY-120,744, englitazone, AD 5075, darglitazone and rosiglitazone.

6. The method according to claim 1, wherein the dried *Dunaliella* algae are administered orally.

7. The method according to claim 1, wherein the *Dunaliella* algae is *Dunaliella bardawil*.

8. The method according to claim 1, wherein the dried *Dunaliella* algae is encapsulated.

* * * * *